(12) United States Patent
Dujardin et al.

(10) Patent No.: US 6,296,865 B1
(45) Date of Patent: Oct. 2, 2001

(54) INSECTICIDE COMPOSITIONS MADE FROM POLYMERS

(75) Inventors: Ralf Dujardin, Novi, MI (US); Mike-Dirk Bublitz, Burscheid (DE); Hermann Neumann, Jakarta (ID)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/117,786

(22) PCT Filed: Feb. 3, 1997

(86) PCT No.: PCT/EP97/00473

§ 371 Date: Aug. 7, 1998

§ 102(e) Date: Aug. 7, 1998

(87) PCT Pub. No.: WO97/29634

PCT Pub. Date: Aug. 21, 1997

(30) Foreign Application Priority Data

Feb. 15, 1996 (DE) ............................................. 196 05 581

(51) Int. Cl.$^7$ ............................ A01N 25/18; A01M 13/00
(52) U.S. Cl. ............................................. 424/409; 424/411
(58) Field of Search ...................................... 424/411, 409

(56) References Cited

U.S. PATENT DOCUMENTS

| | | | |
|---|---|---|---|
| 4,743,448 | * | 5/1988 | Bahadir et al. ........................ 424/411 |
| 5,294,445 | * | 3/1994 | Sieveking et al. .................... 424/411 |
| 5,645,845 | | 7/1997 | Neumann et al. . |

FOREIGN PATENT DOCUMENTS

| | | |
|---|---|---|
| 0 671 123 A1 | 9/1995 | (EP) . |
| 0 693 254 A1 | 1/1996 | (EP) . |
| 2 639 187 | 5/1990 | (FR) . |
| 2 639 188 | 5/1990 | (FR) . |
| 2 070 933 | 9/1981 | (GB) . |

OTHER PUBLICATIONS

English translation of JP Patent No. 890343096 (Sumitomo Chem Ind) Sep. 2, 1991.
English translation of JP Patent No. 780068290 (Fumakila) Dec. 19, 1979.
Derwent Abstract of JP Patent No. 03 200 704 A (Sumitomo Chem Ind) Sep. 2, 1991 (XP002031404).
Derwent Abstract of JP Patent No. 54 160 732 A (Fumakila KK) Dec. 19, 1979 (XP002031419).
Derwent Abstract of JP Patent No. 46 029 010 A (Taisho Pharm Co. Ltd.) (XP002031420).
Derwent Abstract of JP Patent No. 55 064 501 A (Otsuka Kagaku Yakuhin KK) (XP002031421).
Derwent Abstract of JP No. 53 024 032 A (Japan Synthetic Rubber Co. Ltd.) (XP002031422).

* cited by examiner

Primary Examiner—Peter F. Kulkosky
(74) Attorney, Agent, or Firm—Norris McLaughlin & Marcus

(57) ABSTRACT

The present invention relates to insecticidal compositions based on polymers, processes for their preparation and their use for controlling insects which occur in interior rooms.

8 Claims, 11 Drawing Sheets

FIG. 1

GRAPH 11
Vaporization rate for a polypropylene polymer containing various amounts of transfluthrin at 110°C (DBK heater)
Cycles/day 2x8 h

INSECTICIDE COMPOSITIONS MADE FROM POLYMERS

The invention relates to insecticidal compositions based on polymers, processes for their preparation and their use for controlling insects which occur in interior rooms. These new compositions are characterized in that they contain at least one type of insecticide which is incorporated into a suitable polymer. The compositions are further characterized in that they are able to release the insecticide in a controlled manner at room temperature or optionally at a certain temperature, without the shape and macroscopic appearance being changed.

It is an object of the present invention to formulate insecticidal active compounds in such a way that they are not only stable on storage but can also be vaporized in a controlled manner at room temperature or optionally by warming. In this way, a very high activity and duration of action are achieved with low energy consumption. The use of these new insecticidal compositions should be carried out without using a customary container, by standing up the polymeric shaped body containing the active compound without warming, or heating it directly in a suitable vaporization apparatus.

In the case of killing, for example, mosquitoes using an electrical heating apparatus, known as a platelet vaporizer, it is known that suitable materials such as cellulose or cotton board, asbestos or ceramic are impregnated with pyrethroid insecticides to give insecticide plates. The insecticides are volatilized by the action of a heating apparatus which generates a temperature of 120–190° C. A similar principle forms the basis of a gel vaporizer, where insecticides are incorporated into a gel formulation.

Another method of controlling, for example, mosquitoes is the use of liquid vaporizers in which an insecticidal liquid formulation is continuously vaporize by warming via a wick system.

Considerable disadvantages of these platelet, gel or liquid vaporizers result from the fact that vaporization accelerators and other formulation auxiliaries have to be incorporated into the insecticidal composition to prevent thermal decomposition of the active compounds, and also the necessity of using organic solvents in the manufacture.

A further considerable disadvantage of all these known vaporization principles is the fact that the user can come into contact with the active compound or the active compound formulation, for example if the liquid formulation leaks out in the case of liquid vaporizers or the paper platelet is swallowed in the case of platelet vaporizers.

A further disadvantage of the known vaporizer systems mentioned is the nonuniform active compound release characteristics.

In addition, in the case of platelet vaporizers the duration of action is limited to at most 12 hours.

The present invention provides new insecticidal compositions based on polymers which do not have the above-mentioned disadvantages and, in addition, are simple to use, for example in known vaporizer apparatuses as are employed for gel vaporizers (EP 0 693 254 A1 (U.S. Pat. No. 5,645,845)). A continuous release rate of the active compound for up to 60 days, preferably up to 45 days, is ensured without warming or optionally at a low working temperature from 60 to 150° C., preferably 80–120° C.

The insecticidal compositions of the invention comprise mixtures containing at least one type of a pyrethroid insecticide and at least one polymer having a crystallite melting range between 100 and 300° C., preferably between 150 and 250° C., particularly preferably between 150 and 200° C. The softening range is determined by the glass transition temperature in the case of amorphous thermoplastic polymers and by the melting point in the case of partially crystalline polymers. In addition, organic or inorganic auxiliaries such as stabilizers, dyes or fragrances can be incorporated as further additives into the mixtures.

The insecticidal compositions of the invention are prepared by introducing a thermoplastic polymer as granules or powder into a suitable extruder at a suitable temperature and plasticizing it. Under the typical plasticizing conditions and temperatures for the polymer selected, the active compound is introduced directly into the polymer melt by means of a suitable metering-in device and is uniformly distributed in the polymer melt.

The polymer compositions are plasticized by kneading in variable shearing roller extruders, in kneaders (Banbury or Werner und Pfleiderer) in single-screw and twin-screw extruders or special kneaders. The shearing roller extruder is used mainly for batch production, while the incorporation of the additives is carried out continuously using single-screw or twin-screw extruders or Buss-KO kneaders. Suitable extruders or kneaders for incorporating the additives are based on the principle of friction; the heat of friction is achieved by the horizontal back and forth motion of the screws. The screws differ in thread depths, thread widths, pitch in the direction of rotation, depending on polymer/additive mixture. The quality of the homogenization can be adjusted by the kneading time and the ratio of length to diameter of the extruder screws. Good homogenization and plasticization is a prerequisite for the further processing of the active compound-containing polymer compositions.

To obtain homogeneous plasticizable products for thermoplastic processing to give molding compositions, the materials have to be added in a particular form. The thermoplastic is added in granule or powder form. The active compound is added as a solid or liquid depending on the accuracy required by means of volumetric or gravimetric metering devices. Volumetric metering devices are screw, compartmented wheel, rotating disk or vibrating channel feeders. Gravimetric metering devices are feed belt balances or differential feed balances. For free-flowing polymer granules (particle size >50 $\mu$m), metering devices used are vibrating channels, spiral or leaf screws and belts. The active compounds having powder sizes between 10 and 50 $\mu$m are treated like liquids and preferably metered in using "chamber systems" such as compartmented wheels or double screws. The active compounds can be fed into the filling zone of the extruder or further downstream in one or more stages. They are metered into the molten thermoplastics to avoid the formation of secondary agglomerates.

Liquid active compounds are treated differently when added to thermoplastics. Liquid active compounds are added in the premix (heating/cooling mixers). Wax-like active compounds are first melted at 60–80° C. and stored in a heated reservoir before they are fed to the extruder. Liquid active compounds are metered in using gear pumps, screw spindle pumps or single-piston or multipiston pumps. They are fed to the extruder at a point where the melt is under pressure. The pressure in the melt has to be above the vapor pressure of the active compound at the respective temperature of the melt, since otherwise vapor and foam are produced. At the injection point, the pressure should drop in the direction of the point of the screw, i.e. the pressure gradient should be negative, so that the active compound fed in is not squeezed out upstream. In the case of larger amounts of active compounds and large viscosity differences between thermoplastic melt and liquid active compound, it is advantageous to inject the liquid simultaneously at a plurality of points. In the case of thermally sensitive active compounds, the distribution of the active compound in the melt can be achieved more rapidly in this way. It is important that the liquid active compounds are embedded as directly as possible into the melt and are not only injected at the edge of the internal wall of the barrel. Film formation of low-viscosity liquids at the barrel wall has to be avoided by reducing the rate of addition, since otherwise the conveyance of material in the extruder is impaired or can even break down in the case of single-screw extruders. This has to be taken into account particularly for high active compound contents. In this case, use should be made of injection valves which project into the screw channel. The land of the screw is then interrupted at the injection point. When turning off the metering pump, it is absolutely necessary to prevent thermoplastic melt from penetrating into the injection valve and the feed line, solidifying there and blocking the liquid feed when the metering pump is switched on again. To avoid this effect, use is made of special spring-loaded nonreturn valves in which the backflow barrier is located directly at the outlet.

For the liquid active compounds, essentially the same applies in terms of the quantity of the mixing-in process as for the solid active compounds. However, since the liquids metered in are in most cases significantly less viscous than the thermoplastic melt, the problem of dispersing them during homogenization no longer occurs. Essentially, they only have to be dispersed. Suitable devices for this purpose are mixing rings, since these give a dividing-up and spreading-out of the individual layers repeated many times. The same quality of mixing can also be achieved by means of static mixing elements installed between feed screw and die.

Liquid or solid active compounds can also be metered in in the form of additive concentrates. The concentrates are intermediates containing the active compounds in a high concentration embedded in carrier substances. The carrier substance can here be the desired polymer or a material immiscible with the polymer (polymer, filler). In final use, the intermediate is rediluted to the desired low concentration by mixing in further polymer granules. The active compounds highly concentrated in this form have the task of being readily metered active compound concentrates for the setting of different concentrations. These "masterbatches" are usually in granule form.

The thermoplastics containing the active compound can be granulated in various ways. It is possible to either cut extruded and completely or partially cooled extrudates (extrudate granulation) or to cut the hot melt directly on exit from the nozzle before the cap (e.g. water ring granulation).

The active compound-containing granules prepared are further processed thermoplastically to give shaped bodies or processed with further thermoplastic polymers to give mixtures (masterbatch).

For the shaping procedure, use is made of the processes customarily employed for plastics, for example injection molding, extrusion blowing, film extrusion or deep drawing.

As pyrethroid active compounds, preference is given to using:

1) natural pyrethrum,
2) 3-allyl-2-methyl-cyclopent-2-en-4-on-1-yl d/l-cis/trans-chrysanthemate (allethrin/Pynamin®),
3) 3-allyl-2-methyl-cyclopent-2-en-4-on-1-yl d-cis/trans-chrysanthemate (Pynamin forte®),
4) d-3-allyl-2-methyl-cyclopent-2-en-4-on-1-yl d-trans-chrysanthemate (Exrin®),
5) 3-allyl-2-methyl-cyclopent-2-en-4-on-1-yl d-trans-chrysanthemate (Bioallethrin®),
6) N-(3,4,5,6-tetrahydrophthalimido)-methyl dl-cis/trans-chrysanthemate (phthalthrin, Neopynamin®),
7) 5-benzyl-3-furylmethyl d-cis/trans-chrysanthemate (resmethrin, Chrysron forte®),
8) 5-(2-propargyl)-3-furylmethyl chrysanthemate (Furamethrin®),
9) 3-phenoxybenzyl 2,2-dimethyl-3-(2,2-dichlorovinyl)-cyclopropanecarboxylate (permethrin, Exmin®),
10) phenoxybenzyl d-cis/trans-chrysanthemate (phenothrin, Sumithrin®),
11) α-cyanophenoxybenzyl isopropyl-4-chlorophenylacetate (fenvalerate, Sumicidin®),
12) (S)-α-cyano-3-phenoxybenzyl (1R,cis)-3-(2,2-dichlorovinyl)-2,2-dimethylcyclopropanecarboxylate,
13) (R,S)-α-cyano3-phenoxybenyl (1R,1S)-cis/trans-3-(2,2-dichlorovinyl)-2,2-dimethylcyclopropanecarboxylate,
14) α-cyano-3-phenoxybenzyl d-cis/trans-chrysanthemate,
15) 1-ethinyl-2-methyl-2-pentenyl cis/trans-chrysanthemate,
16) 1-ethinyl-2-methyl-2-pentenyl 2,2-dimethyl-3-(2-methyl-1-propenyl)-cyclopropane-1-carboxylate,
17) 1-ethinyl-2-methyl-2-pentenyl 2,2,3,3-tetramethylcyclopropanecarboxylate,
18) 1-ethinyl-2-methyl-2-pentenyl 2,2-dimethyl-3-(2,2-dichlorovinyl)-cyclopropane-1-carboxylate,
19) 2,3,5,6-tetrafluorobenzyl (+)-1R-trans-2,2-dimethyl-3-(2,2-dichlorovinyl)-cyclopropanecarboxylate (transfluthrin, Bayothrin®)

or mixtures of these active compounds.

Particular preference is given to using the active compounds 3-allyl-2-methyl-cyclopent-2-en-4-on-1-yl d-cis/trans-chrysanthemate (Pynamin forte®) and 2,3,5,6-tetrafluorobenzyl (+)-1R-trans-2,2-dimethyl-3-(2,2-dichlorovinyl)-cyclopropanecarboxylate (transfluthrin).

As polymeric materials, preference is given to using amorphous and partially crystalline polymers and also mixtures of the two which can be processed thermoplastically, i.e. as viscous melts and whose softening range is below the boiling point at atmospheric pressure of the active compounds to be, incorporated. The polymers are selected for the appropriate active compound such that the active compound mixes at least partially with the polymers.

As suitable amorphous polymers, preference is given to using:

PVC (plasticized), polystyrene, styrene-butadiene, styrene-acrylonitrile, acrylonitrile-butadiene-styrene, polymethyl acrylate, amorphous polycycloolefins, cellulose esters, aromatic polycarbonates, amorphous aromatic polyamides, polyphenylene ethers, polyether sulfones, polyimides.

As suitable partially crystalline polymers, preference is given to using:

polyethylene, polypropylene, polybutylene, PVC (RIGID), polyamide, polyetheramides, polyesteramides, polyoxymethylene, polyethylene terephthalate, polybutylene terephthalate, polyimide, polyether ether ketone and polyurethane.

Examples of preferred mixtures are:

Blends of polycarbonates with polybutylene terephthalate, blends of polyamide-6 and styrene-acrylonitrile.

Particular preference is given to polypropylene, amorphous aromatic polyamides, aromatic polycarbonates and aromatic polyurethanes.

The insecticidal compositions of the invention can be stabilized by means of antioxidants, by mixing a UV absorber as additive into the formulation. UV absorbers which can be used are all known UV absorbers.

Preference is given to using phenol derivatives such as butylhydroxytoluene (BHT), butylhydroxyanisole (BHA), bisphenol derivatives, arylamines such as phenyl-α-naphthylamine, phenyl-β-naphthylamine, a condensate of phenetidine and acetone or the like or benzophenones.

It is possible to use colorants such as inorganic pigments, e.g. iron oxide, titanium oxide, ferrocyanide blue and inorganic dyes such as alizarin, azo and metal phthalocyanine dyes and metal salts such as salts of iron, manganese, boron, copper, cobalt, molybdenum and zinc.

Furthermore, it is possible to add natural fragrances to the formulations of the invention, for example musk, civet, ambergris, castoreum and similar fragrances: ajowan oil, almond oil, ambrette seed oil absol., angelica root oil, anisole, basil oil, bay oil, benzoin resinoid, bergamot essence, birch oil, rosewood oil, esparto absol., cajeput oil, cananga oil, capsicum oil, caraway oil, cardamon oil, carrot seed oil, cassia oil, cedarwood oil, celery seed oil, cinnamon oil, citronella oil, muscatel sage oil, clove oil, cognac essence, coriander oil, cubeb oil, camphor oil, dill oil, tarragon oil, eucalyptus oil, fennel oil sweet, calbanum resinoid, garlic oil, geranium oil, ginger oil, grapefruit oil, hop oil, hyacinth absol., jasmine absol., juniper oil, labdanum resinoid, lavender oil, bay leaf oil, lemon oil, lemongrass oil, lovage oil, mace oil, mandarin oil, misoma absol., myrrh absol., mustard oil, narcissus absol., neroli oil, nutmeg oil, oak moss absol., olibanum resinoid, onion oil, opoponax resinoid, orange oil, orange blossom oil, orris oil, pepper oil, peppermint oil, Peru balsam, petitgrain oil, fir needle oil, rose absol., rose oil, rosemary oil, sandalwood oil, sage oil, curled mint oil, styrax oil, thyme oil, tolu balsam, tonka bean absol., tuberose absol., terpentine oil, vanilla absol., vetiver oil, violet flower absol., cananga oil and similar plant oils, etc.

Synthetic fragrances which can be added to the formulations of the invention are:

pinene, limonene and similar hydrocarbons; 3,3,5-trimethylcyclohexanol, linalool, geraniol, nerol, citronellol, menthol, borneol, borneylmethoxycyclohexanol, benzyl alcohol, anise alcohol, cinnamyl alcohol, β-phenylethyl alcohol, cis-3-hexanol, terpineol and similar alcohols; anetholes, musk xylol, isoeugenol, methyleugenol and similar phenols; α-amylcinnamaldehyde, anisaldehyde, n-butyraldehyde, cuminaldehyde, cyclamenaldehyde, decylaldehyde, isobutyraldehyde, hexylaldehyde, heptylaldehyde, n-nonylaldehyde nonadienol, citral, citronellal, hydroxy-citronellal, benzaldehyde, methylnonylacetaldehyde, cinnamaldehyde, dodecanol, α-hexylcinnamaldehyde, undecanal, heliotropin, vanillin, ethylvanillin and similar aldehydes, methyl amyl ketone, methyl β-naphthyl ketone, methyl nonyl ketone, musk ketone, diacetyl, acetylpropionyl, acetylbutyryl, carvone, methone, camphor, acetophenone, p-methylacetophenone, ionone, methylionone and similar ketones; amylbutyrolactone, diphenyl oxide, methyl phenylglycidate, nonylacetone, cumarin, cineol, ethyl methyl phenylglycidate and similar lactones or oxides, methyl formate, isopropyl formate, linalyl formate, ethyl acetate, octyl acetate, methyl acetate, benzyl acetate, cinnamyl acetate, butyl propionate, isoamyl acetate, isopropyl isobutyrate, geranyl isovalerate, allyl capronate, butyl heptanoate, octyl caprylate, methyl heptinecarboxylate, methyl octinecarboxylate, isoamyl caprylate, methyl laurate, ethyl myristate, methyl myristate, ethyl benzoate, benzyl benzoate, methylcarbinyl phenylacetate, isobutyl phenylacetate, methyl cinnamate, styracin, methyl salicylate, ethyl anisate, methyl anthrilate, ethyl pyruvate, ethyl α-butylbutyrate, benzyl propionate, butyl acetate, butyl butyrate, p-tert-butylcyclohexyl acetate, cedryl acetate, citronellyl acetate, citronellyl formate, p-cresyl acetate, ethyl butyrate, ethyl caproate, ethyl cinnamate, ethyl phenylacetate, ethylene brassylate, geranyl acetate, geranyl formate, isoamyl salicylate, isoamyl valerate, isobornyl acetate, linalyl acetate, methyl anthranilate, methyl dihydro-jasmonate, nonyl acetate, β-phenylethyl acetate, trichloromethylenephenylcarbinyl acetate, terpinyl acetate, vetiveryl acetate and similar esters. These fragrances can be used individually, or at least two thereof can be used in admixture with one another. Apart from the fragrance, the formulation of the invention may, if desired, additionally contain the additives customary in the fragrances industry, for example patchouli oil or similar volatilization inhibitors, for example eugenol or similar viscosity regulators.

The compositions generally contain between 0.1 and 80% by weight, preferably between 0.2 and 40% by weight, particularly preferably between 1.0 and 20% by weight, of active compound.

BRIEF DESCRIPTION OF THE DRAWINGS

Graph 1 shows the vaporization rate for a cellulose triacetate polymer containing 2% of transfluthrin.

Graph 2 shows the vaporization rate for a polypropylene polymer containing 2% transfluthrin.

Graph 3 shows the vaporization rate for a polstyrene polymer containing 2% transfluthrin.

Graph 4 shows the vaporization rate for a polynorbornene polymer containing 2% transfluthrin.

Graph 5 shows the vaporization rate for a cellulose triacetate polymer containing 1.8% of Pynamin Forte.

Graph 6 shows the vaporization rate for a polycarbonate polymer containing 2% transfluthrin.

Graph 7 shows the vaporization rate for a polypropylene polymer containing 1.8% of Pynamin Forte.

Graph 8 shows the vaporization rate for a thermoplastic polyurethane triacetate polymer containing 2% transfluthrin.

The preparation and use of the compositions of the invention is illustrated by the following examples:

EXAMPLE 1

Compounding of active compounds in various polymers

Compounding was carried out on a twin-screw instrumented extruder BRABENDR PLASTICORDER PL 2000 (extruder model: 35/17 D, extruder cooling: air, inlet cooling: water, 3 mm round extrusion nozzle, four electrically heated heating zones).

The polymer granules are metered into the extruder at the respective temperature via an Engelhardt balance. The active compound is warmed in a steam-heated reservoir and pumped in via a gear pump (Ismatec). The throughput is set at a total of 6 kg/h.

The polymer extrudate formed is cooled in a water bath and then chopped in a granulator. The granules are dried at about 50° C. in a waterpump vacuum.

Gravimetric tests:

The weighed test specimens are laid in the middle of the intended cold heater and reweighed accurately after the respective 2 cycles. The tests are carried out until the test specimens no longer show a weight loss.

Theoretical vaporizable amount (Test specimen) start×ACC (vaporizable contents or active compound)=theo $m$ (vaporizable amount).

| Example | Polymer | Active compound | Heating zones-temp. (° C.) 1 | 2 | 3 | 4 | Die | Torque [Nm] | Pressure [bar] | Rotational speed [l/min] |
|---|---|---|---|---|---|---|---|---|---|---|
| 1.1. | Cellulose-acetate | Transfluthrin [2%] | 200 | 200 | 200 | 200 | 208 | 26–29 | 23–24 | 60 |
| 1.2. | Poly-urethane | Transfluthrin [2%] | 200 | 200 | 200 | 200 | 207–209 | 36–30 | 37–41 | 60 |
| 1.3. | Poly-ethylene | Transfluthrin [2%] | 200 | 220 | 220 | 220 | 230–235 | 35–37 | 33–35 | 60 |
| 1.4. | Polystyrene | Transfluthrin [2%] | 200 | 210 | 210 | 20 | 219–222 | 30–33 | 23–25 | 60 |
| 1.5. | Poly-propylene | Transfluthrin [2%] | 220 | 240 | 240 | 240 | 251–256 | 49–50 | 37–49 | 60 |
| 1.6. | Poly-norbornene | Transfluthrin [2%] | 240 | 280 | 280 | 280 | 294 | 29–30 | 13 | 60 |
| 1.7. | Poly-carbonate | Transfluthrin [2%] | 240 | 280 | 280 | 280 | 294–295 | 37–38 | 26–28 | 60 |
| 1.8. | Cellulose acetate | Pynamin forte [2%] | 200 | 200 | 200 | 200 | 208 | 26–29 | 23–24 | 60 |
| 1.9. | Poly-ethylene | Pynamin forte [2%] | 200 | 220 | 220 | 220 | 230–235 | 35–37 | 33–35 | 60 |
| 1.10. | Poly-carbonate | Pynamin forte [2%] | 240 | 280 | 280 | 280 | 294–295 | 37–38 | 26–28 | 60 |
| 1.11. | Poly-propylene | Transfluthrin [5%] | 220 | 240 | 240 | 240 | 251–256 | 49–50 | 37–49 | 60 |

EXAMPLE 2

Release behavior of insecticidal compositions based on polymers

Heater:

Working temperature 100° C.: DBK plate heater with PTC HP01-4/09,

Working temperature 110° C.: DBK plate heater with PTC BP01-2/11.

2.1. Comparison of various polymeric materials

Temperature: 110° C.

DBK heating apparatus with PTC

Test specimen: 69 mm×40 mm×1 mm

Cycles: 2×8 h/day

| | Example No. | Material | Active compound | Preparative Example | Weight loss in mg/h Start 8 h | Middle 40 h | End 80 h |
|---|---|---|---|---|---|---|---|
| * | 2.1.1. | Cellulose triacetate | 2% Transfluthrin | 1.1. | 2.7 | 2.7 | 0.3 |
| | 2.1.2. | Poly-propylene | 2% Transfluthrin | 1.5. | 1.26 | 1.3 | 0.1 |
| ** | 2.1.3. | Polystyrene | 2% Transfluthrin | 1.4. | +0.05 | <0.05 | 0 |
| | 2.1.4. | Poly-norbornene | 2% Transfluthrin | 1.6. | +0.1 | 0 | +<0.05 |
| * | 2.1.5. | Cellulose acetate | 2% Pynamin Forte | 1.8. | 2.2 | 0.9 | 0.4 |
| | 2.1.6. | Poly-carbonate | 2% Transfluthrin | 1.7. | 0.2 | 0.1 | 0 |
| | 2.1.7. | Poly-carbonate | 2% Pynamin Forte | 1.10. | 0.2 | 0.1 | 0 |
| | 2.1.8. | Thermo. PU | 2% Transfluthrin | 1.2. | 3.1 | 0.9 | <0.05 |

*The test specimens showed considerable weight gains at intermediate times, these possibly being caused by hygroscopic effects.
**Product showed substantial deformation under the action of heat.
For plots see graphs 1 to 8

2.2. Temperature influence

Gravimetric tests:

The weighed test specimens are laid in the middle of the intended cold heater and reweighed accurately after the respective 2 cycles. The tests are carried out until the test specimens no longer show a weight loss.

Theoretical vaporizable amount (Test specimen) start×ACC (vaporizable contents or active compound)=theo *m* (vaporizable amount).

DBK heating apparatus with PTC

Test specimen: 69 mm×40 mm×1 mm

Cycles: 1×8 h/day

| Example No. | Temp. (° C.) | Material | Active compound | Preparative Example | Weight loss in mg/h |  |  |
|---|---|---|---|---|---|---|---|
| | | | | | Start 8 h | Middle 40 h | End 64 h |
| 2.2.1. | 110 | Polypropylene | 2% Transfluthrin | 1.5. | 2.5 | 0.5 | 0.1 |
| 2.2.2. | 100 | Polypropylene | 2% Transfluthrin | 1.5. | 1.4 | 0.6 | 0.3 |

For plot see graph 9

2.3. Gravimetric theoretical/actual comparison

Gravimetric tests:

The weighed test specimens are laid in the middle of the intended cold heater and reweighed accurately after the respective 2 cycles. The tests are carried out until the test specimens no longer show a weight loss.

Comparison between amount of active compound which can theoretically be present in each test specimen and actual total weight loss.

Temperature: 110° C.

DBK heating apparatus with PTC

Test specimen: 69 mm×40 mm×1 mm

Cycles: 2×8 h/day

| Example No. | Material | Active compound | Preparative Example | Theoretical amount of active compound [mg] | Total loss [mg] | Total loss in [%] |
|---|---|---|---|---|---|---|
| 2.3.1. | Cellulose-triacetate | 2% Transfluthrin | 1.1. | 67.3 | 57.8 | 85.9 |
| 2.3.2. | Polypropylene | 2% Transfluthrin | 1.5. | 49.0 | 47.3 | 96.5 |
| 2.3.3. | Polystyrene | 2% Transfluthrin | 1.4. | 57.1 | 1.8 | 3.2 |
| 2.3.4. | Polynorbornene | 2% Transfluthrin | 1.6. | 57.2 | 0 | 0 |
| 2.3.5. | Cellulose triacetate | 2% Pynamin Forte | 1.8. | 61.5 | 34.5 | 56.1 |
| 2.3.6. | Polycarbonate | 2% Transfluthrin | 1.7. | 63.9 | 3.7 | 5.8 |
| 2.3.7. | Polycarbonate | 2% Pynamin Forte | 1.10. | 59.3 | 2.9 | 4.9 |
| 2.3.8. | Polyurethane | 2% Transfluthrin | 1.2. | 70.5 | 89.9 | 127.5 |

The result for thermoplastic polyurethane, viz. 127%, indicates degradation products (decomposition).

For plot see graph 10

2.4. Concentration influence

Gravimetric tests:

The weighed test specimens are laid in the middle of the intended cold heater and reweighed accurately after the respective 2 cycles. The tests are carried out until the test specimens no longer show a weight loss.

Theoretical vaporizable amount (Test specimen) start×ACC (vaporizable contents or active compound)=theo *m* (vaporizable amount).

DBK heating apparatus with PTC

Test specimen: 69 mm×40 mm×1 mm

Cycles: 1×8 h/day

| Example No. | Temp. [° C.] | Material | Active compound | Preparative Example | Weight loss in mg/h |  |  |  |
|---|---|---|---|---|---|---|---|---|
| | | | | | Start 16 h | 40 h | 64 h | 128 h |
| 2.4.1. | 100 | Polypropylene | 2% Transfluthrin | 1.5. | 1.3 | 0.6 | 0.3 | — |
| 2.4.2. | 100 | Polypropylene | 5% Transfluthrin | 1.11. | 1.5 | 0.8 | 0.4 | 0.4 |

For plot see graph 11

Theoretical vaporizable amount (test specimen) start×ACC (vaporizable contents or active compound)=theo *m* (vaporizable amount).

EXAMPLE 3

Biological results

Testing of vaporizer systems for effect on mosquitoes in 20 m³ rooms.

Figure 1:
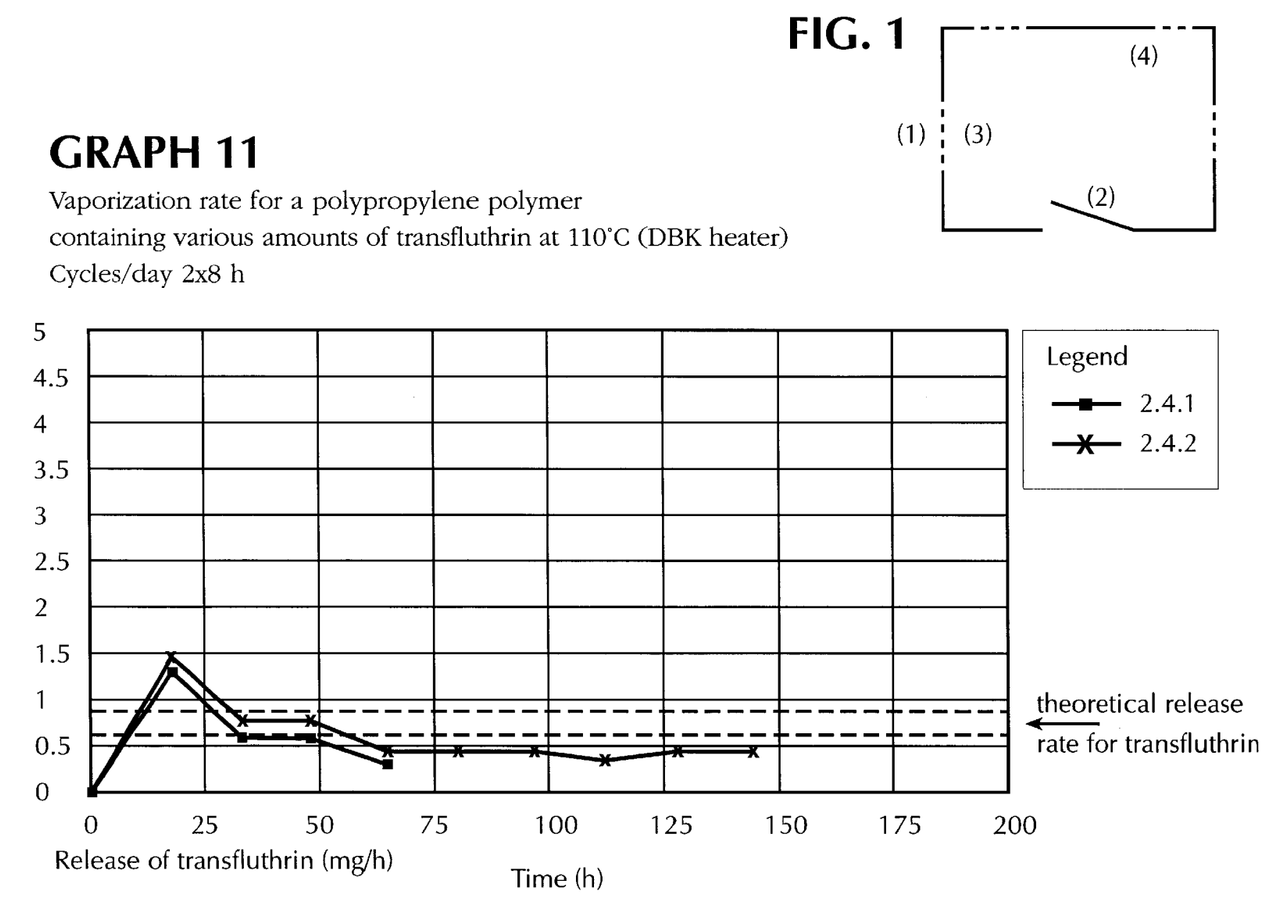

The tests are carried out in 20 m³ (L=2.84 m, W=2.33 m, H=3.03 m) rooms whose inner walls and ceilings are made of stainless steel (DIN 4571) with 5 windows (1) per room in each case. [FIG. 1] The floor is tiled with unglazed tiles. 3 wire cages (L=8.5 cm, diam.=8.0 cm, mesh opening =1.0 mm) each containing 20 test animals are hung from the ceiling of the test rooms at a height of 1.70 m, 0.45 m from the respective wall (positions (2), (3) and (4). Under these, a further cage is positioned at a height of 0.8 m on a stand at each of positions (3) and (4).

The electrically operated vaporizer system is placed on the floor in the middle of the room, the room is closed and the little oven is started up. The operating time is 8 hours and during this time it is determined from the outside through the windows when 10%, 50%, 95% and 100% of the mosquitoes are knocked down in the individual cages. The test animals remain in the rooms for 8 hours. The percentage of the animals which have fallen on their backs (KD) is then determined. All animals are taken from the cages and transferred to insecticide-free clear plastic beakers. The beakers are closed with perforated lids and provided with cellulose swabs soaked with 10% strength sugar solution. After the test animals have been kept for 24 hours in an insecticide-free atmosphere, the mortality is determined.

At the end of the test, the heated vaporizer vessel is removed from the room and the latter is aired with 200 air changes/hour. The vaporizer vessel is stored at room temperature.

EXAMPLE 3.1

Testing of Example 1.5 in 20 m³ rooms against mosquitoes of the species *Aedes aegypti*, sensitive.
DBK heating apparatus with PTC
Heater temperature: 110° C.
Test specimen: 69 mm×40 mm×1 mm
2% of transfluthrin in polypropylene
Room temperature: 24° C.
relative humidity: from 50 to 76%

| Operating time for batch/test after days | Test height | Heater 1 % knock down after hours (h) and minutes (') | | | | % Mortality | | Heater 2 % knock down after hours (h) and minutes (') | | | | % Mortality | |
|---|---|---|---|---|---|---|---|---|---|---|---|---|---|
| (hours) | cm | KD 10 | KD 50 | KD 95 | KD 100 | 8 h | 24 h | KD 10 | KD 50 | KD 95 | KD 100 | 8 h | 24 h |
| 0 days | 170 | 14' | 17' | 22' | 24' | 100 | 100 | 15' | 17' | 21' | 23' | 100 | 100 |
|  | 80 | 15' | 18' | 21' | 22' | 100 | 100 | 16' | 18' | 21' | 22' | 100 | 100 |
| 1 day | 170 | 19' | 21' | 25' | 27' | 100 | 100 | 22' | 26' | 28' | 32' | 100 | 100 |
| (8 h) | 80 | 25' | 37' | 41' | 46' | 100 | 100 | 26' | 33' | 39' | 41' | 100 | 100 |
| 2 days | 170 | 22' | 26' | 31' | 34' | 100 | 100 | 22' | 26' | 31' | 35' | 100 | 100 |
| (16 h) | 80 | 29' | 35' | 40' | 43' | 100 | 100 | 31' | 38' | 45' | 47' | 100 | 100 |
| 3 days | 170 | 24' | 28' | 32' | 34' | 100 | 100 | 25' | 28' | 32' | 35' | 100 | 100 |
| (24 h) | 80 | 31' | 37' | 40' | 42' | 100 | 100 | 34' | 39' | 42' | 45' | 100 | 100 |
| 4 days | 170 | 24' | 27' | 34' | 36' | 100 | 100 | 35' | 39' | 45' | 48' | 100 | 100 |
| (32 h) | 80 | 33' | 38' | 42' | 46' | 100 | 100 | 39' | 44' | 49' | 52' | 100 | 100 |
| 5 days | 170 | 32' | 38' | 46' | 49' | 100 | 100 | 37' | 43' | 49' | 53' | 100 | 100 |
| (40 h) | 80 | 40' | 45' | 52' | 56' | 100 | 100 | 43' | 50' | 55' | 58' | 100 | 100 |
| 6 days | 170 | 40' | 47' | 55' | 59' | 100 | 100 | 53' | 1h00' | 1h12' | 1h19' | 100 | 100 |
| (48 h) | 80 | 51' | 57' | 1h01' | 1h06' | 100 | 100 | 49' | 56' | 1h01' | 1h09' | 100 | 100 |
| 7 days | 170 | 58' | 1h08' | 1h19' | 1h24' | 100 | 100 | 1h07' | 1h23' | 1h40' | 1h50' | 100 | 100 |
| (56 h) | 80 | 1h09' | 1h22' | 1h35' | 1h40' | 100 | 100 | 1h08' | 1h27' | 1h46' | 1h59' | 100 | 100 |

EXAMPLE 3.2

Testing of Example 1.5 in 20 m³ rooms against mosquitoes of the species *Culex quinquefasciatus*, resistant.
DBK heating apparatus with PTC
Heater temperature: 110° C.
Test specimen: 69 mm×40 mm×1 mm
2% of transfluthrin in polypropylene
Room temperature: 24° C.
relative humidity: from 50 to 76%

| Operating time for batch/test after days | Test height | Heater 1 % knock down after hours (h) and minutes (') | | | | % Mortality | | Heater 2 % knock down after hours (h) and minutes (') | | | | % Mortality | |
|---|---|---|---|---|---|---|---|---|---|---|---|---|---|
| (hours) | cm | KD 10 | KD 50 | KD 95 | KD 100 | 8 h | 24 h | KD 10 | KD 50 | KD 95 | KD 100 | 8 h | 24 h |
| days | 170 | 35' | 41' | 49' | 57' | 100 | 100 | 39' | 44' | 56' | 1h05' | 100 | 100 |
|  | 80 | 41' | 48' | 58' | 1h08' | 100 | 100 | 41' | 55' | 1h06' | 1h12' | 100 | 100 |

-continued

| | | Heater 1 | | | | | | Heater 2 | | | | |
|---|---|---|---|---|---|---|---|---|---|---|---|---|
| Operating time for batch/test after days | Test height | % knock down after hours (h) and minutes (') | | | | % Mortality | | % knock down after hours (h) and minutes (') | | | | % Mortality | |
| (hours) | cm | KD 10 | KD 50 | KD 95 | KD 100 | 8 h | 24 h | KD 10 | KD 50 | KD 95 | KD 100 | 8 h | 24 h |
| 1 day | 170 | 49' | 1h05' | 1h16' | 1h38' | 100 | 100 | 1h08' | 1h32' | 1h56' | 2h15' | 100 | 100 |
| (8 h) | 80 | 1h05' | 1h39' | 2h04' | 2h17' | 100 | 100 | 1h26' | 2h05' | 2h39' | 3h00' | 100 | 100 |
| 2 days | 170 | 1h26' | 1h45' | 2h03' | 2h19' | 100 | 100 | 1h50' | 2h16' | 2h35' | 2h54' | 100 | 100 |
| (16 h) | 80 | 1h33' | 1h53' | 2h27' | 2h40' | 100 | 100 | 1h41' | 2h15' | 2h40' | 3h08' | 100 | 100 |
| 3 days | 170 | 1h31' | 1h49' | 2h15' | 2h32' | 100 | 100 | 1h53' | 2h21' | 2h51' | 3h08' | 100 | 100 |
| (24 h) | 80 | 2h10' | 2h31' | 2h49' | 3h02' | 100 | 100 | 2h14' | 2h41' | 3h22' | 3h38' | 100 | 100 |
| 4 days | 170 | 1h41' | 2h13' | 2h41' | 3h05' | 100 | 100 | 2h06' | 2h46' | 3h44' | 3h57' | 100 | 100 |
| (32 h) | 80 | 2h19' | 2h47' | 3h17' | 3h36' | 100 | 100 | 2h47' | 3h54' | 4h35' | 5h12' | 100 | 100 |
| 5 days | 170 | 2h17' | 3h09' | 4h43' | 5h44' | 100 | 100 | 2h57' | 4h21' | 6h30' | 7h24' | 100 | 100 |
| (40 h) | 80 | 2h36' | 4h02' | 4h58' | 5h37' | 100 | 100 | 3h50' | 5h35' | 7h15' | >8h | 98 | 100 |
| 6 days | 170 | 4h02' | 5h20' | >8h | >8h | 97 | 100 | 5h52' | >8h | >8h | >8h | 65 | 72 |
| (48 h) | 80 | 4h01' | 6h22' | 7h48' | >8h | 95 | 100 | 6h26' | >8h | >8h | >8h | 53 | 25 |
| 7 days | 170 | 6h50' | >8h | >8h | >8h | 32 | 65 | >8h | <8h | >8h | >8h | 8 | 27 |
| (56 h) | 80 | 7h15' | >8h | >8h | >8h | 13 | 50 | >8h | >8h | >8h | >8h | 5 | 10 |

Vaporization rates during biological testing:
DBK heating apparatus with PTC
Room temperature: 24° C.
Heater temperature: 110° C.
Test specimen: 69 mm×40 mm×1 mm
2% of transfluthrin in polypropylene
relative humidity:
from 50 to 76%

| | Heater 1 | | Heater 2 | |
|---|---|---|---|---|
| Operating time (hours) | Vaporization rate/ day (mg) | Vaporized amount, total (mg) | Vaporization rate/ day (mg) | Vaporized amount, total (mg) |
| 8 | 20.1 | 20.1 | 21.0 | 21.0 |
| 16 | 7.9 | 28.0 | 9.6 | 30.6 |
| 24 | 9.6 | 37.6 | 8.0 | 38.6 |
| 32 | 5.3 | 42.9 | 5.4 | 44.0 |
| 40 | 2.4 | 45.3 | 3.3 | 47.3 |
| 48 | 1.8 | 47.1 | 1.5 | 48.8 |
| 56 | 1.0 | 48.1 | 1.0 | 49.8 |
| 64 | 0.6 | 48.7 | 0.9 | 50.7 |

What is claimed is:

1. Insecticidal compositions comprising (i) an insecticide selected from the group consisting of transfluthrin, at least one 3-allyl-2-methyl-cyclopent-2-en-4on-1yl chrysanthemate and mixtures thereof, in combination with (ii) a polypropylene polymer having a crystallite melting range between 100–300° C., wherein said insecticide (i) is released at a temperature of from 60 to 150° C.

2. Insecticidal composition according to claim 1, further comprising stabilizers, colorants or fragrances.

3. Insecticidal composition according to claim 1, wherein said insecticide is 3-alkyl-2-methyl-cyclopent-2-en-4-on-1-yl d-cis/trans-chrysanthemate.

4. A method for killing mosquitoes in a room, which comprises placing an insecticidal composition according to claim 1 in said room and heating it.

5. The method of claim 4 wherein said composition is heated to a temperature of 60° C. to 150° C.

6. The method of claim 5 wherein said temperature is a temperature of 80° C. to 120° C.

7. The method of claim 4 wherein said composition is heated in a vaporization apparatus and said insecticide is vaporized.

8. The insecticidal composition of claim 1, wherein said insecticide is transfluthrin.

* * * * *

UNITED STATES PATENT AND TRADEMARK OFFICE
CERTIFICATE OF CORRECTION

PATENT NO.    : 6,296,865 B1
DATED         : October 2, 2001
INVENTOR(S)   : Ralf Dujardin et al.

It is certified that error appears in the above-identified patent and that said Letters Patent is hereby corrected as shown below:

<u>Column 13,</u>
Line 52, change "en-4on-1yl…" to -- en-4-on-1-yl… --

Signed and Sealed this

Eighth Day of April, 2003

JAMES E. ROGAN
*Director of the United States Patent and Trademark Office*